US009763904B2

United States Patent
Alken et al.

(10) Patent No.: US 9,763,904 B2
(45) Date of Patent: *Sep. 19, 2017

(54) POSITION-SPECIFIC ASYMMETRIC DEUTERIUM ENRICHED CATECHOLAMINE DERIVATIVES AND MEDICAMENTS COMPRISING SAID COMPOUNDS

(71) Applicant: Teva Pharmaceuticals International GmbH, Jona (CH)

(72) Inventors: Rudolf-Giesbert Alken, Svedala (SE); Frank Schneider, Berlin (DE)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,343

(22) Filed: Jan. 10, 2017

(65) Prior Publication Data

US 2017/0119716 A1    May 4, 2017

Related U.S. Application Data

(63) Continuation of application No. 14/765,430, filed as application No. PCT/EP2014/052267 on Feb. 5, 2014, now Pat. No. 9,567,289.

(60) Provisional application No. 61/760,738, filed on Feb. 5, 2013.

(51) Int. Cl.
| | |
|---|---|
| A61K 31/198 | (2006.01) |
| A61K 9/28 | (2006.01) |
| A61K 9/20 | (2006.01) |
| A61K 31/277 | (2006.01) |
| A61K 31/165 | (2006.01) |

(52) U.S. Cl.
CPC .......... *A61K 31/198* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2813* (2013.01); *A61K 9/2853* (2013.01); *A61K 9/2866* (2013.01); *A61K 31/165* (2013.01); *A61K 31/277* (2013.01)

(58) Field of Classification Search
None
See application file for complete search history.

(56) References Cited

U.S. PATENT DOCUMENTS

2006/0135615 A1   6/2006   Alken

FOREIGN PATENT DOCUMENTS

| WO | WO 2004/056724 | 7/2004 |
| WO | WO 2007/093450 | 8/2007 |

OTHER PUBLICATIONS

Foster, "Deuterium Isotope Effects in the Metabolism of Drugs and Xenobiotics: Implications for Drug Design", Advances in Drug Research, vol. 14, pp. 1-40, 1985.
International Preliminary Report on Patentability in Corresponding International Patent Application No. PCT/EP2014/052267, dated Aug. 20, 2015.
International Search Report in corresponding International Patent Application No. PCT/EP2014/052267, dated Feb. 6, 2014.
Malmof et al., Deuterium Substitutions in the L-Dopa Molecule Improve its anti-akinetic Potency without Increasing Dyskinesias Experimental Neurology, vol. 225, pp. 408-415, 2010.
Oba et al., "Stereo-Divergent Synthesis of L-threo- and L-erythro [2,3-$^2$H$_2$]amino acids using optically active dioxopiperazine as a chiral template" J. Chem. Soc., Perkin Trans., pp. 1275-1281, Jan. 1, 1998.

*Primary Examiner* — Brian J Davis
(74) *Attorney, Agent, or Firm* — Baker Hostetler LLP

(57) ABSTRACT

Herein described are deuterated catecholamine derivatives of the general Formula I

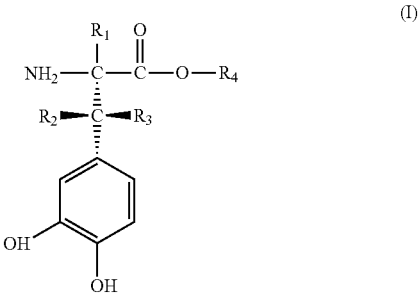

(I)

wherein, $R_1$ is deuterium, $R_2$, and $R_3$ are independently selected from hydrogen and deuterium and wherein at least one of $R_2$ and $R_3$ has a deuterium enrichment in the range from 0.02 mol % to 100 mol % deuterium, and wherein the deuterium enrichment of $R_2$ and $R_3$ is different from each other and that the difference between the deuterium enrichment of $R_2$ and $R_3$ is at least 5 percentage points, $R_4$ is hydrogen, deuterium, $C_1$ to $C_6$-alkyl or $C_5$ to $C_6$-cycloalkyl, deuterated $C_1$ to $C_6$-alkyl or $C_5$ to $C_6$-cycloalkyl, or a group that is easily hydrolytically or enzymatically cleavable under physiological conditions, as well as their physiologically acceptable salts and their stereoisomers, enantiomers or diastereomers in optically pure form. The compounds can easily be prepared by mixing deuterated and non-deuterated compounds in a predefined ratio. The compounds show anti-Parkinson effect at lower doses and show lower side effects.

22 Claims, No Drawings

POSITION-SPECIFIC ASYMMETRIC DEUTERIUM ENRICHED CATECHOLAMINE DERIVATIVES AND MEDICAMENTS COMPRISING SAID COMPOUNDS

This application is a continuation of U.S. patent application Ser. No. 14/765,430, filed Aug. 3, 2015, which is a U.S. national stage, filed under 35 U.S.C. §371, of International Patent Application No. PCT/EP2014/052267, filed Feb. 5, 2014, which claims priority to U.S. Provisional Application No. 61/760,738, filed Feb. 5, 2013. These priority applications are incorporated by reference herein.

The present invention relates to position-specific asymmetric deuterium enriched catecholamine derivatives, methods for their production and medicaments comprising said compounds, as well as their use in the treatment of Parkinson's disease.

Known representatives of catecholamines, such as L-DOPA (levodopa) as well as their carboxylic acid esters, are utilized, among other things, for the treatment of Parkinson's disease and restless leg syndrome. Such a pharmaceutical which contains levodopa is, for example, Dopaflex®. L-DOPA acts on the dopamine concentration in neurons of the brain. Unlike dopamine itself, it can pass through the blood-brain barrier and is converted into dopamine in the brain.

In addition, levodopa is administered in combination with active additives in pharmaceuticals. Combinations of levodopa are used with peripheral decarboxylase inhibitors, with inhibitors of the enzyme catechol-O-methyltransferase (COMT), with inhibitors of the enzyme monoamine oxidase (MAO) and with dopamine β-hydroxylase inhibitors.

In this connection, the decarboxylase inhibitors used are, for example: D,L-serine-2-(2,3,4-trihydroxybenzyl) hydrazide (benserazide), (−)-L-α-hydrazino-3,4-dihydroxy-α-methylhydrocinnamic acid (carbidopa), L-serine-2-(2,3,4-trihydroxybenzyl)hydrazide, glycine-2-(2,3,4-trihydroxybenzyl) hydrazide and L-tyrosine-2-(2,3,4-trihydroxybenzyl)hydrazide. Examples of combination preparations of levodopa and decarboxylase inhibitors include, among others: Madopar® (levodopa and benserazide hydrochloride) as well as Nacom® (levodopa and carbidopa).

Examples of COMT inhibitors are entacapone (Comtan®) and cabergoline, and frequently used MAO inhibitors are selegiline hydrochloride, moclobemide and tranylcypromine.

Calcium 5-butyl picolinate and calcium 5-pentyl picolinate are described as inhibitors for dopamine-β-hydroxylase (DE-A 2 049 115).

Parkinson's disease is a neurodegenerative disease with a slow progressive course characterized by different symptoms and signs that may be present or develop during the progression of disease. Core symptoms are bradykinesia and at least one of the following: resting tremor, muscular rigidity and postural reflex impairment. Other symptoms that may occur during the disease progression are autonomic disturbances, sleep disturbances, disturbances in the sense of smell or sense, of temperature as well as depressive symptoms and cognitive dysfunctions.

The improvement of the impaired dopaminergic neurotransmission by administration of L-DOPA is the backbone of the current pharmacotherapy. Patients with advanced Parkinson's disease require higher doses of dopaminergics but this is limited by motor complications, like fluctuations and involuntarily movements (described as levodopa induced dyskinesia, LIDs). Fluctuations might be due to the shorter striatal persistence (half-life) of dopamine especially in advanced Parkinson's disease patients, also referred to as "Parkinson's patients". A clinical established approach to prolong striatal dopamine persistence is the co-administration of MAO-B inhibitors which block the main metabolic breakdown route of dopamine. The induction of LIDs is associated in many patients with higher CNS dopamine levels generated by large L-DOPA doses. Currently there are different pharmacological means under development to treat existing LIDs.

α,β,β-D3-L-DOPA exhibited higher longer-lasting striatal dopamine levels than L-DOPA. Correspondingly to the increased availability of dopamine in the striatum, α, β,β-D3-L-DOPA showed improved motor activity compared to L-DOPA in several Parkinson models (Malmlöf et al., Exp Neurol, 2008, 538-542; Malmlöf et al., Exp Neurol, 2010, 225: 408-415). The equi-effective dose of α, β,β-D3-L-DOPA compared to L-DOPA was about 60%. The observed longer striatal persistence of dopamine allowed the assumption that fluctuations might be reduced as well.

S/S-2-amino-2,3-dideutero-3-(3,4-dihydroxyphenyl)propionic acid (α, β-D2-L-DOPA) and L-2-amino-2,3,3-trideutero-3-(3,4-dihydroxyphenyl)propionic acid (α, β,β-D3-L-DOPA) were shown to increase and prolong the output of striatal dopamine significantly more than L-DOPA (WO-A 2004/056724 and WO-A 2007/093450).

The highest striatal dopamine concentrations were found after administration of α, β-D2-L-DOPA. Those dopamine levels were even higher than those after the administration of the triple-deuterated α, β,β-D3-L-DOPA which included the same deuterated positions as the double deuterated L-DOPA.

At the equi-effective dose (same striatal dopamine levels and same motor effect as L-DOPA), α, β,β-D3-L-DOPA caused significant less dyskinesia than L-DOPA (Malmlöf et al., Exp Neurol, 2010, 225: 408-415).

The problem to be solved according to the invention is to improve the activity of the known α, β,β-D3-L-DOPA.

As used herein and in the context of the present invention the meaning of "deuterated" is extended to partially or completely deuterated compounds. "Completely deuterated" compounds are compounds in which at least 98 mol % deuterium are present in the respective position within the chemical compound (The deviation to 100 Mol % is caused by analytical measurement deviation and experimental errors.) This means that there has been achieved an enrichment of deuterium in the respective position and that hydrogen has been replaced. The respective enrichment may be performed by chemical reaction in that one uses deuterated starting materials in chemical reactions or that an hydrogen/deuterium exchange has been performed by mixing respective compounds.

"Deuterated" is therefore not related to any naturally occurring deuterium in hydrogen compounds. As it is known, deuterium is present in hydrogen in natural abundance to an extend of 0.015 mol %. Any abundance or enrichment that is greater than 0.02 mol % is understood as being "deuterated" in the sense of this present invention.

The problem is solved according to the invention by providing deuterated catecholamine derivatives of the general Formula I:

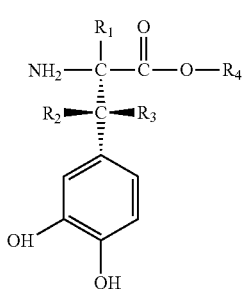

(I)

wherein $R_1$ is deuterium, $R_2$, and $R_3$ are independently selected from hydrogen and deuterium and wherein at least one of $R_2$ and $R_3$ has a deuterium enrichment in the range from 0.02 mol % to 100 mol % deuterium, and wherein the deuterium enrichment of $R_2$ and $R_3$ is different from each other and that the difference between the deuterium enrichment of $R_2$ and $R_3$ is at least 5 percentage points, $R_4$ is hydrogen, deuterium, $C_1$ to $C_6$-alkyl or $C_5$ to $C_6$-cycloalkyl, deuterated $C_1$ to $C_6$-alkyl or $C_5$ to $C_6$-cycloalkyl, or a group that is easily hydrolytically or enzymatically cleavable under physiological conditions, as well as their physiologically acceptable salts and their stereoisomers, enantiomers or diastereomers in optically pure form.

Deuterated catecholamine derivatives, according to the invention are preferred, wherein the difference between the deuterium enrichment of $R_2$ and $R_3$ is at least 7 percentage points.

Deuterated catecholamine derivatives, according to the invention are preferred, wherein the difference between the deuterium enrichment of $R_2$ and $R_3$ is at least 10 percentage points.

Deuterated catecholamine derivatives, according to the invention are preferred, wherein the difference between the deuterium enrichment of $R_2$ and $R_3$ is at least 15 percentage points.

Deuterated catecholamine derivatives, according to the invention are preferred, wherein the difference between the deuterium enrichment of $R_2$ and $R_3$ is at least 20 percentage points.

Deuterated catecholamine derivatives, according to the invention are preferred, wherein $R_4$ is selected from the group comprising hydrogen, deuterium, methyl, perdeuteromethyl, ethyl, perdeuteroethyl, propyl, perdeuteropropyl, butyl, perdeuterobutyl, $C_1$ to $C_6$-alkyl, that may be branched or unbranched, or $C_5$ to $C_6$-cycloalkyl, deuterated or partly deuterated $C_1$ to $C_6$-alkyl, that may be branched or unbranched, or deuterated or partly deuterated $C_5$ to $C_6$-cycloalkyl.

Deuterated catecholamine derivatives, according to the invention are preferred, wherein $R_4$ is selected from the group comprising hydrogen, deuterium, methyl, perdeuteromethyl, ethyl, perdeuteroethyl, propyl, perdeuteropropyl, cyclohexyl, and perdeuterocyclohexyl.

Deuterated catecholamine derivatives, according to the invention are preferred, wherein $R_4$ is hydrogen.

Deuterated catecholamine derivatives, according to the invention are preferred, wherein $R_4$ is methyl.

Deuterated catecholamine derivatives, according to the invention are preferred, wherein $R_4$ is ethyl.

Especially preferred according to the present invention is L-2-amino-2,3,3*-trideutero-3-(3,4-dihydroxyphenyl) propionic acid (α, β,β-D3-L-DOPA), wherein 3* indicates that the deuterium enrichment in one β-position is about 90 mol %. This compound has according to the definition of the present invention a difference in the deuterium enrichment in the β-positions of about 8 to 10 percentage points. The other positions carrying deuterium are completely deuterated and show a deuterium enrichment of at least 98 mol %. This compound is named Test Item D in Tables 1 and 2 as outlined in the present description herein.

The problem is also solved by providing deuterated catecholamine derivatives, obtainable by admixing a compound of general Formula II

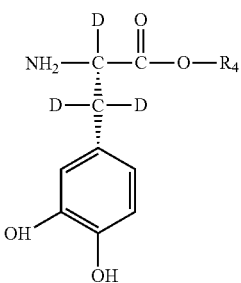

(II)

with a compound of general Formula III or general Formula IV

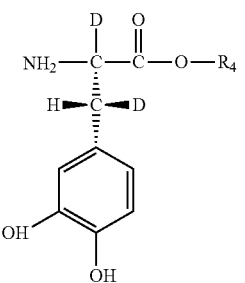

(III)

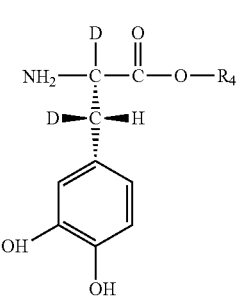

(IV)

wherein, in general Formula II, III, or IV, $R_4$ is hydrogen, deuterium, $C_1$ to $C_6$-alkyl or $C_5$ to $C_6$-cycloalkyl, deuterated $C_1$ to $C_6$-alkyl or $C_5$ to $C_6$-cycloalkyl, or a group that is easily hydrolytically or enzymatically cleavable under physiological conditions, as well as their physiologically acceptable salts and their stereoisomers, enantiomers or diastereomers in optically pure form, in a ratio to adjust the deuterium enrichment in position $R_2$ or $R_3$ in general Formula I within the predefined range of 0.02 mol % to 100 mol % deuterium.

Preferred are, according to the present invention, deuterated catecholamine derivatives, wherein the compound according to general Formula II is selected from the list comprising L-2-amino-2,3,3-trideutero-3-(3,4-dihydroxyphenyl) propionic acid, L-2-amino-2,3,3-trideutero-3-(3,4-dihydroxyphenyl) methyl propionate, L-2-amino-2,3,3-trideutero-3-(3,4-dihydroxyphenyl) ethyl propionate, L-2-amino-2,3,3-trideutero-3-(3,4-dihydroxyphenyl) propyl propionate, L-2-amino-2,3,3-trideutero-3-(3,4-dihydroxyphenyl) cyclohexyl propionate, L-2-amino-2,3,3-trideutero-3-(3,4-dihydroxyphenyl) perdeuteromethyl propionate, L-2-amino-2,3,3-trideutero-3-(3,4-dihydroxyphenyl) perdeuteroethyl propionate, L-2-amino-2,3,3-trideutero-3-(3,4-dihydroxyphenyl) perdeuteropropylethyl propionate, L-2-amino-2,3,3-trideutero-3-(3,4-dihydroxyphenyl) perdeuterocyclohexyl propionate, as well as their physiologically acceptable salts and their stereoisomers, enantiomers or diastereomers in optically pure form, and wherein the compound according to general Formula III or general Formula IV is selected from the list comprising L-2-amino-2,3-dideutero-3-(3,4-dihydroxyphenyl) propionic acid, L-2-amino-2,3-dideutero-3-(3,4-dihydroxyphenyl) methyl propionate, L-2-amino-2,3-dideutero-3-(3,4-dihydroxyphenyl) ethyl propionate, L-2-amino-2,3-dideutero-3-(3,4-dihydroxyphenyl) propyl propionate, L-2-amino-2,3-dideutero-3-(3,4-dihydroxyphenyl) cyclohexyl propionate, L-2-amino-2,3-dideutero-3-(3,4-dihydroxyphenyl) perdeuteromethyl propionate, L-2-amino-2,3-dideutero-3-(3,4-dihydroxyphenyl) perdeuteroethyl propionate, L-2-amino-2,3-dideutero-3-(3,4-dihydroxyphenyl) perdeuteropropylethyl propionate, L-2-amino-2,3-dideutero-3-(3,4-dihydroxyphenyl) perdeuterocyclohexyl propionate, as well as their physiologically acceptable salts and their stereoisomers, enantiomers or diastereomers in optically pure form.

Especially preferred are deuterated catecholamine derivatives, wherein the percentage of the compound according to general Formula II is in the range of 0.1 mol % to 99.9 mol %, preferably in the range of 5 mol % to 95 mol %, especially preferred in the range of 78 mol % to 95 mol %. Most preferred are herein deuterated catecholamine derivatives, wherein the percentage of the compound according to general Formula II is in the range of 88 mol % to 92 mol %. Most preferred are herein also deuterated catecholamine derivatives, wherein the percentage of the compound according to general Formula II is in the range of 78 mol % to 82 mol %.

Therefore, according to the invention a mixture is preferred in which 90 mol % of L-2-amino-2,3,3-trideutero-3-(3,4-dihydroxyphenyl) propionic acid are admixed with 10 mol % of L-2-amino-2,3-dideutero-3-(3,4-dihydroxyphenyl) propionic acid, or in which 80 mol % of L-2-amino-2,3,3-trideutero-3-(3,4-dihydroxyphenyl) propionic acid are admixed with 20 mol % of L-2-amino-2,3-dideutero-3-(3,4-dihydroxyphenyl) propionic acid, or in which 85 mol % of L-2-amino-2,3,3-trideutero-3-(3,4-dihydroxyphenyl) propionic acid are admixed with 15 mol % of L-2-amino-2,3-dideutero-3-(3,4-dihydroxyphenyl) propionic acid, or in which 70 mol % of L-2-amino-2,3,3-trideutero-3-(3,4-dihydroxyphenyl) propionic acid are admixed with 30 mol % of L-2-amino-2,3-dideutero-3-(3,4-dihydroxyphenyl) propionic acid.

A further object of the present invention is a method for the preparation of deuterated catecholamine derivatives according to the present invention, by mixing (i) a compound according to general Formula I:

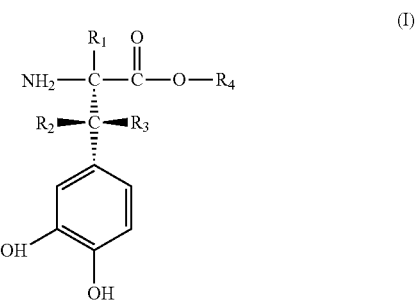

wherein $R_1$, $R_2$, $R_3$, and $R_4$ have the meaning as given above, as well as their physiologically acceptable salts and their stereoisomers, enantiomers or diastereomers in optically pure form, wherein the deuterium enrichment of $R_2$ and $R_3$ is different from each other and that the difference between the deuterium enrichment of $R_2$ and $R_3$ has a first predefined value with (ii) at least one compound according to general Formula I:

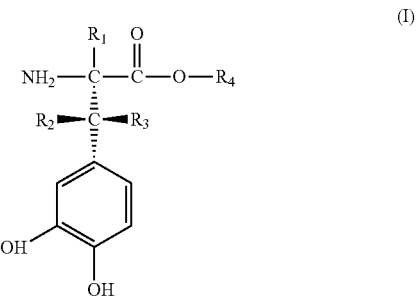

wherein $R_1$, $R_2$, $R_3$, and $R_4$ have the meaning as above, as well as their physiologically acceptable salts and their stereoisomers, enantiomers or diastereomers in optically pure form, wherein the deuterium enrichment of $R_2$ and $R_3$ is different from each other and that the difference between the deuterium enrichment of $R_2$ and $R_3$ has a second predefined value, (iii) in a ratio that yields a predefined difference between the deuterium enrichment of $R_2$ and $R_3$, which is in the range from at least 5 to at least 20 percentage points.

A further object of the present invention is the use of the deuterated catecholamine derivatives according to the invention as well as physiologically acceptable salts thereof, for the treatment of dopamine deficiency diseases or diseases which are based on disrupted tyrosine transport or disrupted tyrosine decarboxylase, such as Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy.

Preferred is the use of the deuterated catecholamine derivatives according to the invention as well as physiologically acceptable salts thereof, in combination with an enzyme inhibitor or several enzyme inhibitors, for the treatment of dopamine deficiency diseases or diseases which are based on disrupted tyrosine transport or disrupted tyrosine decarboxylase, such as Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy.

Preferred is the use of the deuterated catecholamine derivatives according to the invention as well as physiologically acceptable salts thereof, further characterized in that the enzyme inhibitor or the enzyme inhibitors involve decarboxylase inhibitors and/or catechol-O-methltransferase inhibitors and/or monoamine oxidase inhibitors and/or β-hydroxylase inhibitors.

Preferred is the use of the deuterated catecholamine derivatives according to the invention as well as physiologically acceptable salts thereof, further characterized in that the decarboxylase inhibitor is selected from the group consisting of D,L-serine-2-(2,3,4-trihydroxybenzyl) hydrazide (benserazide), (+L-α-hydrazino-3,4-dihydroxy-α-methylhydrocinnamic acid (carbidopa), L-serine-2-(2,3,4-trihydroxybenzyl) hydrazide, glycine-2-(2,3,4-trihydroxybenzyl) hydrazide and L-tyrosine-2-(2,3,4-trihydroxybenzyl) hydrazide as well as physiologically acceptable salts thereof.

Preferred is the use of the deuterated catecholamine derivatives according to the invention as well as physiologically acceptable salts thereof further characterized in that the catechol-O-methyltransferase inhibitor is selected from entacapone and cabergoline as well as physiologically acceptable salts thereof.

Preferred is the use of the deuterated catecholamine derivatives according to the invention as well as physiologically acceptable salts thereof, further characterized in that the monoamine oxidase inhibitor is selected from the group consisting of selegiline, moclobemide and tranylcypromine as well as physiologically acceptable salts thereof.

Preferred is the use of the deuterated catecholamine derivatives according to the invention as well as physiologically acceptable salts thereof, further characterized in that the β-hydroxylase inhibitor is selected from calcium 5-butyl picolinate and calcium 5-pentyl picolinate as well as physiologically acceptable salts thereof.

Preferred is the use of the deuterated catecholamine derivatives according to the invention as well as physiologically acceptable salts thereof, for the production of pharmaceuticals for the treatment of Parkinson's disease, restless leg syndrome, of amyotrophic lateral sclerosis and of multiple system atrophy.

A further object of the present invention is a pharmaceutical composition, which contains deuterated catecholamines according to the invention as well as physiologically acceptable salts thereof, for the treatment of Parkinson's disease, of restless leg syndrome, of dystonia, for inhibiting prolactin secretion, for stimulating the release of growth hormone, for the treatment of neurological symptoms of chronic manganese intoxications, of amyotrophic lateral sclerosis and of multiple system atrophy, in addition to pharmaceutically acceptable adjuvants and additives.

Preferred is a pharmaceutical composition, which comprises deuterated catecholamines according to the invention as well as physiologically acceptable salts thereof, for the treatment of Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy, as well as one or more enzyme inhibitors, in addition to pharmaceutically acceptable adjuvants and additives.

Preferred is a pharmaceutical composition, which comprises deuterated catecholamines according to the invention, further characterized in that the enzyme inhibitor or the enzyme inhibitors involve decarboxylase inhibitors and/or catechol-O-methyltransferase inhibitors and/or monoamine oxidase inhibitors and/or β-hydroxylase inhibitors.

Preferred is a pharmaceutical composition, which comprises deuterated catecholamines according to the invention, further characterized in that the decarboxylase inhibitor is selected from the group consisting of D,L-serine-2-(2,3,4-trihydroxybenzyl) hydrazide (benserazide), (–)-L-α-hydrazino-3,4-dihydroxy-α-methylhydrocinnamic acid (carbidopa), L-serine-2-(2,3,4-trihydroxybenzyl) hydrazide, glycine-2-(2,3,4-trihydropxybenzyl) hydrazide and L-tyrosine-2-(2,3,4-trihydroxybenzyl) hydrazide as well as physiologically acceptable salts thereof.

Preferred is a pharmaceutical composition, which comprises deuterated catecholamines according to the invention, further characterized in that the catechol-O-methyltransferase inhibitor is selected from entacapone and cabergoline as well as physiologically acceptable salts thereof.

Preferred is a pharmaceutical composition, which comprises deuterated catecholamines according to the invention, further characterized in that the monoamine oxidase inhibitor is selected from the group consisting of selegiline, moclobemide and tranylcypromine as well as physiologically acceptable salts thereof.

Preferred is a pharmaceutical composition, which comprises deuterated catecholamines according to the invention, further characterized in that the β-hydroxylase inhibitor is selected from calcium 5-butyl picolinate and calcium 5-pentyl picolinate as well as physiologically acceptable salts thereof.

Still another object of the present invention is a pharmaceutical composition, which comprises a mixture of 10 mol % of L-2-amino-2,3-dideutero-3-(3,4-dihydroxyphenyl) propionic acid as well as physiologically acceptable salts thereof, and 90 mol % of L-2-amino-2,3,3-trideutero-3-(3,4-dihydroxyphenyl) propionic acid as well as physiologically acceptable salts thereof, in a pharmacologically active amount, optionally in addition with pharmaceutically acceptable adjuvants and additives.

Preferred is a pharmaceutical composition, wherein the composition further comprises, in a pharmacologically active amount, carbidopa, benserazide or entacapone or a mixture of the said compounds.

The pharmaceutical compositions of the present invention are very powerful in the treatment of Parkinson's disease as the asymmetric position specific deuterium enrichment can tune the known effects of position specific deuterated L-DOPA. This provides a powerful tool to adjust the treatment according to the symptoms and side effects that change during disease progression.

According to the stage of Parkinson's disease in the respective person, one can use a compounds with a deuterium enrichment adjusted to the need of the patient under treatment. This offers new opportunities for a medication that is tailor-made or customized to the patient.

Another object of the present invention is a method for the treatment of dopamine deficiency diseases or diseases which are based on disrupted tyrosine transport or disrupted tyrosine decarboxylase, such as Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy with a person who has been identified as a person who is in the need of the treatment of dopamine deficiency diseases or diseases which are based on disrupted tyrosine transport or disrupted tyrosine decarboxylase, such as Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy, the method comprising administering to the person deuterated catecholamine derivatives according to the invention as given in general formula as well as physiologically acceptable salts thereof.

Preferred is the method, wherein the administering to the person is in combination with an enzyme inhibitor or several enzyme inhibitors.

Preferred is the method, wherein the enzyme inhibitor or the enzyme inhibitors involve decarboxylase inhibitors and/ or catechol-O-methyltransferase inhibitors and/or monoamine oxidase inhibitors and/or β-hydroxylase inhibitors.

Preferred is the method, wherein the decarboxylase inhibitor is selected from the group consisting of D,L-serine-2-(2,3,4-trihydroxybenzyl) hydrazide (benserazide), (−)-L-α-hydrazino-3,4-dihydroxy-α-methylhydrocinnamic acid (carbidopa), L-serine-2-(2,3,4-trihydroxybenzyl)hydrazide, glycine-2-(2,3,4-trihydroxybenzyl)hydrazide and L-tyrosine-2-(2,3,4-trihydroxybenzyl)hydrazide as well as physiologically acceptable salts thereof.

Preferred is the method, wherein the catechol-O-methyltransferase inhibitor is selected from entacapone and cabergoline as well as physiologically acceptable salts thereof.

Preferred is the method, wherein the monoamine oxidase inhibitor is selected from the group consisting of selegiline, moclobemide and tranylcypromine as well as physiologically acceptable salts thereof.

Preferred is the method, wherein the β-hydroxylase inhibitor is selected from calcium 5-butyl picolinate and calcium 5-pentyl picolinate as well as physiologically acceptable salts thereof.

The preparation of the deuterated catecholamine derivatives of the present invention can be performed in at least two principal ways. One way is to mix compounds with a certain deuterium enrichment with compounds which have only hydrogen or only a highly enriched (>98% D) deuterium substitution at a certain position. By mixing at least two compounds any required enrichment level of deuterium at any position can be obtained. The other way of preparation is to add specifically enriched starting material to a certain step during the preparation process of the compounds according to the invention.

The preparation of deuterium enriched catecholamine derivatives is known from WO-A 2004/056724 and WO-A 2007/093450. In there, the preparation of selectively deuterated DOPA derivatives is disclosed that have a deuterium enrichment in the respective position within the molecule of at least 98%.

One preferred synthetic pathway is shown in Scheme 1.

Scheme 1: Synthetic pathway to deuterated catecholamine derivatives

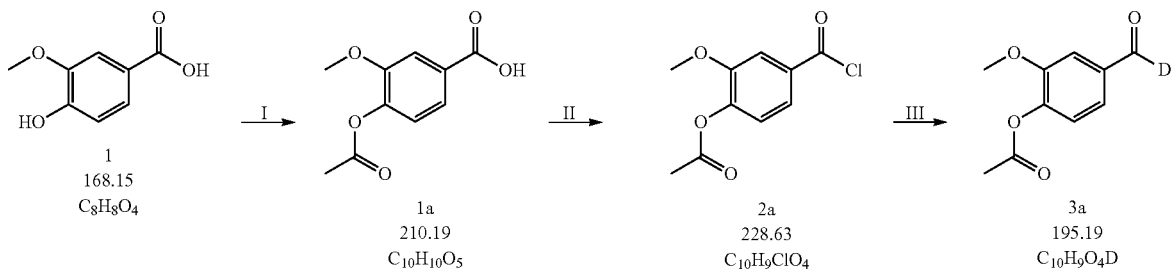

1
168.15
$C_8H_8O_4$ 1a
210.19
$C_{10}H_{10}O_5$ 2a
228.63
$C_{10}H_9ClO_4$ 3a
195.19
$C_{10}H_9O_4D$

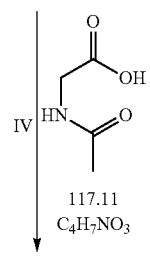

IV 117.11
$C_4H_7NO_3$

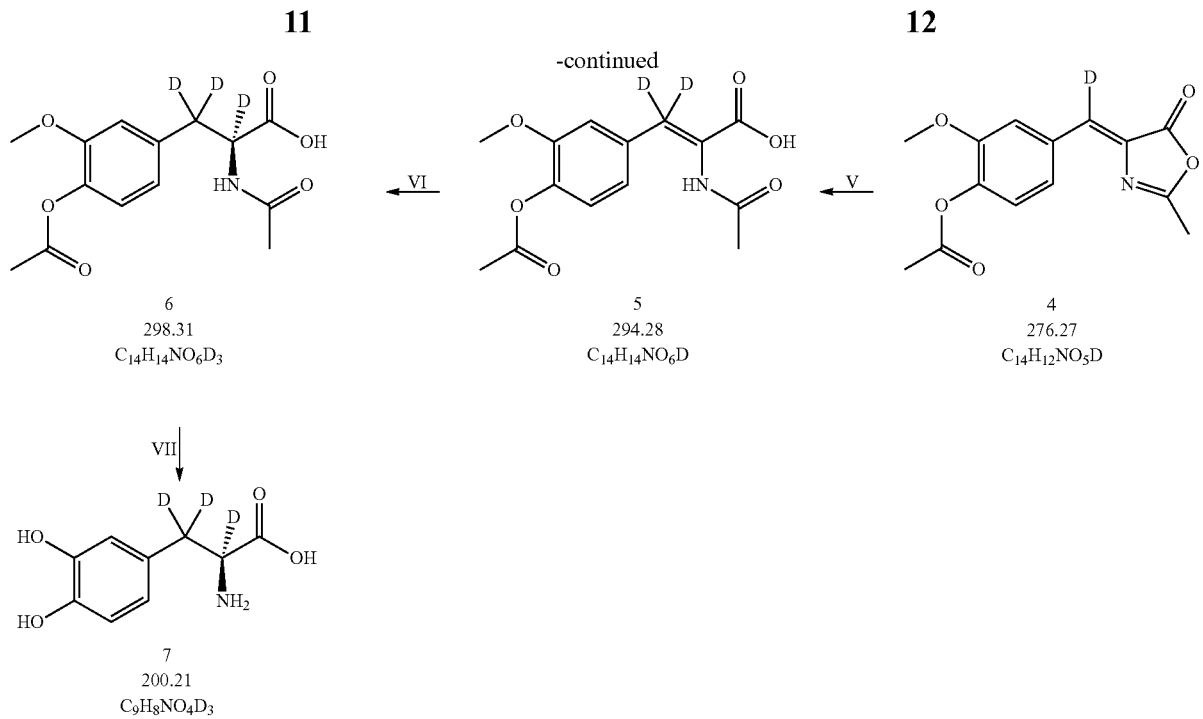

According to the present invention it is preferred to prepare the compounds according to the invention by adding non-deuterated educts 3a and/or 4 and/or 5 to the respective deuterated compounds. The ratio of deuterated and non-deuterated compounds is adjusted in such a manner to obtain the desired ratio in the end product. This method of production has the advantage that no further mixing steps are required. This obtained product is then by definition no longer a mixture.

For the production of the physiologically acceptable salts of the deuterated catecholamine derivatives according to the invention, the usual physiologically acceptable inorganic and organic acids such as hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid can be used. Additional acids that can be used are described, for example, in Fortschritte der Arzneimittelforschung, Vol. 10, pp. 224-225, Birkhäuser Publishers, Basel and Stuttgart, 1966, and Journal of Pharmaceutical Sciences, Vol. 66, pp. 1-5 (1977).

The acid addition salts are usually obtained in a way known in and of itself by mixing the free base or solutions thereof with the corresponding acid or solutions thereof in an organic solvent, for example, a lower alcohol, such as methanol, ethanol, n-propanol or isopropanol or a lower ketone such as acetone, methyl ethyl ketone or methyl isobutyl ketone or an ether such as diethyl ether, tetrahydrofuran or dioxane. For better crystal precipitation, mixtures of the named solvents can also be used. In addition, physiologically acceptable aqueous solutions of acid addition salts of the compounds used according to the invention can be produced therefrom in an aqueous acid solution.

The acid addition salts of the compounds according to the invention can be converted to the free base in a way known in and of itself, e.g., with alkali or ion exchangers. Additional salts can be obtained from the free base by reaction with inorganic or organic acids, particularly those which are suitable for the formation of salts that can be employed therapeutically. These or also other salts of the compound according to the invention, such as, e.g., the picrate, may also serve for purification of the free base by converting the free base into a salt, separating this salt, and afterwards releasing the base from the salt.

The subject of the present invention is also pharmaceuticals for oral, buccal, sublingual, nasal, rectal, subcutaneous, intravenous or intramuscular application as well as for inhalation, which, in addition to the usual vehicle and dilution agents, also contain a compound of general Formula I or the acid addition salt thereof as an active ingredient.

The pharmaceuticals of the invention are produced, in the known way and with suitable dosage, with the usual solid or liquid vehicle substances or dilution agents and the commonly used pharmaceutical-technical adjuvants corresponding to the desired type of application. The preferred preparations consist of a form for administration which is suitable for oral application. Such forms of administration include, for example, tablets, sucking tablets, film tablets, dragees, capsules, pills, powders, solutions, aerosols or suspensions or slow-release forms.

Of course, parenteral preparations such as injection solutions are also considered. In addition, suppositories, for example, have also been named as preparations. Corresponding tablets can be obtained, for example, by mixing the active substance with known adjuvants, for example, inert dilution agents such as dextrose, sugar, sorbitol, mannitol, polyvinylpyrrolidone, bursting agents such as corn starch or alginic acid, binders such as starches or gelantins, lubricants such as magnesium stearate or talc and/or agents for achieving a slow-release effect such as carboxypolymethylene, carboxymethylcellulose, cellulose acetate phthalate or polyvinyl acetate. The tablets may also consist of several layers.

Dragees can also be produced correspondingly, for controlled or delayed release forms of preparation, by coating the cores produced analogously to the tablets with agents commonly used in dragee coatings, for example, polyvinylpyrrolidone or shellac, gum arabic, talc, titanium dioxide or sugar. The dragee envelope may also consist of several layers, wherein the adjuvants mentioned above in the case of tablets can be used.

Solutions or suspensions containing the active substance used according to the invention may additionally contain agents that improve taste, such as saccharin, cyclamate or sugar, as well as, e.g., taste enhancers such as vanilla or orange extract. They may also contain suspension adjuvants such as sodium carboxymethylcellulose or preservatives such as p-hydroxybenzoate. Capsules containing active substances can be produced, for example, by mixing the active substance with an inert vehicle such as lactose or sorbitol and encapsulating this mixture in gelatin capsules. Suitable suppositories can be produced, for example, by mixing with vehicle agents provided therefore, such as neutral fats or polyethylene glycol or derivatives thereof The production of the pharmaceutical preparations according to the invention is known in the art, and is described in handbooks known to the person skilled in the art, for example, Hager's Handbuch [Handbook] (5th ed.) 2, 622-1045; List et al., Arzneiformenlehre [Instructions for Drug Forms], Stuttgart: Wiss. Verlagsges. 1985; Sucker et al., Pharmazeutische Technologie [Pharmaceutical Technology], Stuttgart: Thieme 1991; Ullmann's Enzyklopädie [Encyclopedia] (5th ed.) A 19, 241-271; Voigt, Pharmazeutische Technologie [Pharmaceutical Technology], Berlin: Ullstein Mosby 1995.

The following examples shall explain the present invention. The examples shall be understood only as a preferred embodiment of the invention. It is not intended to limit the present invention to the scope of the given examples.

EXAMPLE 1

The effects on motor performance and the development of dyskinesia following administration of deuterated L-DOPA derivatives with different deuterium enrichment at specific position of the side chain have been compared among each other and to L-DOPA in the 6-hydroxydopamine (6-OHDA) rodent model of Parkinson's disease. The tested compounds and the specific deuterium enrichment of these compounds are displayed in Table 1.

TABLE 1

Test Items

| Name | Deuterium Enrichment | | |
|---|---|---|---|
| | α | $\beta_R$ | $\beta_S$ |
| A L-2-amino-3-(3,4-dihydroxyphenyl) propionic acid (L-DOPA) | NA | NA | NA |
| B S/S-2-amino-2,3-dideutero-3-(3,4-dihydroxyphenyl) propionic acid (α,β-D2-L-DOPA) | >98% | <1% | >98% |
| C L-2-amino-2,3,3-trideutero-3-(3,4-dihydroxyphenyl) propionic acid (α,β,β-D3-L-DOPA) | >98% | >98% | >98% |
| D L-2-amino-2,3,3*-trideutero-3-(3,4-dihydroxyphenyl) propionic acid (α,β,β*-D3-L-DOPA) | >98% | 90% | >98% |

(3* or β*, respectively, indicates that the position is not completely deuterated)
($\beta_R$ and $\beta_S$ relate to the commonly used R/S nomenclature indicating the relative positions in optically active compounds)

Female Sprague-Dawley rats weighing approximately 225 g were housed on a 12-hour light/dark cycle and kept on standard laboratory diet and water ad libitum. The rats were lesioned by unilateral injection of the neurotoxin 6-OHDA. The lesion was validated by measuring the rotational activity after i.p. injection of 2.5 mg/kg D-amphetamine.

The anti-Parkinson effect (effect on motor performance) was evaluated by measurement of drug induced contralateral rotations. A dose effect was established to determine the equipotent (equi-effective) dose.

Dyskinesia was evaluated after repeated treatment by scoring the animals for abnormal involuntary movements. The rats were scored, by an observer blinded to the experimental design for limb, axial and orolingual involuntary movements.

The equipotent dose as percent of L-DOPA dose that caused the same effect on motor performance and dyskinesia observed following repeated administration of these doses is shown in Table 2.

TABLE 2

Results

| Test Item | Equipotent Dose [% of L-DOPA dose] | Motor Effect [% of L-DOPA effect] | Dyskinesia [% of dyskinesia caused by L-DOPA] |
|---|---|---|---|
| A | 100% | 100% | 100% |
| B | 30% | 100% | 100% |
| C | 60% | 100% | 50% |
| D | 35% | 100% | 50% |

The effect of α, β-D2-L-DOPA [B] on motor performance is significantly greater compared to α, β, β-D3-L-DOPA [C] and L-DOPA [A] as reflected by a lower equipotent dose. However dyskinesia after α, β-D2-L-DOPA [B] is not reduced in comparison to L-DOPA at equipotent dose whereas α, β, β-D3-L-DOPA [C] caused significantly less dyskinesia than L-DOPA at equipotent dose.

Surprisingly, test item D with almost 100% deuterium enrichment in position α and $\beta_S$ and 90% in position $\beta_R$ provides both a motor effect equivalent to the di-deuterated α, β-D2-L-DOPA [B] and a reduction of dyskinesia as the triple-deuterated α, β, β-D3-L-DOPA [C].

Test compound D is thus the optimal treatment for late stage Parkinson patients suffering from motor fluctuations and LIDs and requiring high doses of L-DOPA.

The example of compound D shows that asymmetric position specific deuterium enrichment can tune the known effects of position specific deuterated L-DOPA. This provides a powerful tool to adjust the treatment according to the symptoms and side effects that change during disease progression.

According to the stage of Parkinson's disease in the respective person, one can use a compounds with a deuterium enrichment adjusted to the need of the patient under treatment. This offers new opportunities for a medication that is tailor-made or customized to the patient.

EXAMPLE 2

Preparation of Test Compound D from Table 1
L-2-Amino-2,3,3*-trideutero-3-(3,4-dihydroxyphenyl) propionic acid (α, β, β-D3-L-DOPA)
Test item D has a deuterium enrichment of 90% in $\beta_R$ position.
D is obtained by mixing 10 mol % L-2-amino-2,3(S)-dideutero-3-(3,4-dihydroxyphenyl) propionic acid with 90 mol % L-2-amino-2,3,3-trideutero-3-(3,4-dihydroxyphenyl)

propionic acid (deuterium enrichment >98% in all three positions). Experimental data for $C_9H_{8.1}{}^2H_{2.9}NO_4$

| Calculated: | H | 6.95 | C | 54.05 | N | 7.00 | O | 32.00 |
|---|---|---|---|---|---|---|---|---|
| Analyt.: | H | 7.00 | C | 54.02 | N | 7.00 | O | 31.98 |

The degree of deuteration has also been determined by NMR spectroscopy. For that purpose NMR spectra with a 500 MHz spectrometer have been recorded. As a solvent, $d_6$-DMSO was used. The following Table 3 shows the respective position within the compound of test item D and the integral (AUC=area under curve) of the registered spectra, reflecting the content of hydrogen at the respective positions.

TABLE 3

NMR results

| Position | Integral (AUC) |
|---|---|
| Ring | 3.02 |
| α | 0.02 |
| β | 0.01 |
| β* | 0.10 |

The preparation of the starting material L-2-amino-2,3,3-trideutero-3-(3,4-dihydroxyphenyl) propionic acid is described in WO-A 2004/056724, the preparation of the starting material L-2-Amino-2,3(S)-dideutero-3-(3,4-dihydroxyphenyl) propionic acid is described in WO-A 2007/093450.

After mixing the compounds the mixture may be processed further in order to obtain a suitable pharmaceutical product for the medication of Parkinson's disease as given in the following examples.

EXAMPLE 3

Tablet with film coating containing α, β,β*-D3-L-DOPA

| Composition of the core: | |
|---|---|
| α,β,β*-D3-L-DOPA (Test Item D) | 40.00 mg |
| Povidone | 20.00 mg |
| Sorbitol | 7.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400 ™ | 2.50 mg |
| Titanium oxide | 3.00 mg |
| Talc | 3.00 mg |

Preparation:

α,β,β*-D3-L-DOPA (Test Item D) and highly dispersed silicon dioxide are granulated in a compulsory mixer with a solution of povidone and sorbitol. The granules are dried, screened, mixed with pregelatinated starch, croscarmellose sodium, carmellose sodium and microcrystalline cellulose, then combined with magnesium stearate and compressed into tablets. The tablets are film coated with hydroxypropylmethylcellulose, Macrogol, titanium dioxide and talc.

EXAMPLE 4

Tablet with film coating containing α,β,β*-D3-L-DOPA and Carbidopa

| Composition of the core: | |
|---|---|
| α,β,β*-D3-L-DOPA (Test Item D) | 35.00 mg |
| Carbidopa | 25.00 mg |
| Povidone | 20.00 mg |
| Sorbitol | 7.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400 ™ | 2.50 mg |
| Titanium oxide | 3.00 mg |
| Talc | 3.00 mg |

Preparation:

α,β,β*-D3-L-DOPA (Test Item D), carbidopa and highly dispersed silicon dioxide are granulated in a compulsory mixer with a solution of povidone and sorbitol. The granules are dried, screened, mixed with pregelatinated starch, croscarmellose sodium, carmellose sodium and microcrystalline cellulose, then combined with magnesium stearate and compressed into tablets. The tablets are film coated with hydroxypropylmethylcellulose, Macrogol, titanium dioxide and talc.

EXAMPLE 5

Tablet with film coating containing microencapsulated α,β,β*-D3-L-DOPA and Carbidopa

| Composition of the core: | |
|---|---|
| α,β,β*-D3-L-DOPA (Test Item D) | 40.00 mg |
| Carbidopa | 25.00 mg |
| Tartaric acid | 5.00 mg |
| Povidone | 20.00 mg |
| Sorbitol | 7.00 mg |
| Eudragit RL ™ solid | 20.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400 ™ | 2.50 mg |
| Titanium oxide | 3.00 mg |
| Talc | 3.00 mg |

Preparation:

α,β,β*-D3-L-DOPA (Test Item D), Carbidopa, sorbitol and Eudragit are microencapsulated and homogenised in a barrel mixer with tartaric acid, highly dispersed silicon dioxide, povidone, pregelatinated starch, croscarmellose sodium, carmellose sodium and microcrystalline cellulose, then combined with magnesium stearate and compressed into tablets. The tablets are film coated with hydroxypropylmethylcellulose, Macrogol, titanium dioxide and talc.

EXAMPLE 6

Tablet with film coating containing microencapsulated α,β,β*-D3-L-DOPA and benserazide

| Composition of the core: | |
|---|---|
| α,β,β*-D3-L-DOPA (Test Item D) | 40.00 mg |
| Benserazide | 25.00 mg |
| Tartaric acid | 5.00 mg |
| Povidone | 20.00 mg |
| Sorbitol | 7.00 mg |
| Eudragit RL™ solid | 20.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400TM | 2.50 mg |
| Titanium oxide | 3.00 mg |
| Talc | 3.00 mg |

The preparation of the film coated tablets is as given in Example 5.

EXAMPLE 7

Tablet with film coating containing α,β,β*-D3-L-DOPA and benserazide

| Composition of the core: | |
|---|---|
| α,β,β*-D3-L-DOPA (Test Item D) | 35.00 mg |
| Benserazide | 25.00 mg |
| Povidone | 20.00 mg |
| Sorbitol | 7.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400 ™ | 2.50 mg |
| Titanium oxide | 3.00 mg |
| Talc | 3.00 mg |

Preparation:

α,β,β*-D3-L-DOPA (Test Item D), carbidopa, and highly dispersed silicon dioxide are granulated in a compulsory mixer with a solution of povidone and sorbitol. The granules are dried, screened, mixed with pregelatinated starch, croscarmellose sodium, carmellose sodium and microcrystalline cellulose, then combined with magnesium stearate and compressed into tablets. The tablets are film coated with hydroxypropylmethylcellulose, Macrogol, titanium dioxide and talc.

EXAMPLE 8

Tablet with film coating containing α,β,β*-D3-L-DOPA and carbidopa and entacapone

| Composition of the core: | |
|---|---|
| α,β,β*-D3-L-DOPA (Test Item D) | 40.00 mg |
| Carbidopa | 25.00 mg |
| Entacapone | 200.00 mg |
| Povidon K30 | 20.00 mg |
| Crospovidone Type B | 15.00 mg |
| Mannitol | 9.00 mg |
| Silicon dioxide, highly dispersed | 2 mg |
| Pregelatinated starch | 40.00 mg |
| Croscarmellose-sodium | 13.30 mg |
| Carmellose-sodium | 20.05 mg |
| Microcrystalline cellulose | 41.00 mg |
| Magnesium stearate | 2.00 mg |
| Film coating: | |
| Hydroxypropylmethylcellulose | 16.00 mg |
| Macrogol 400 ™ | 2.50 mg |
| Titanium oxide | 3.00 mg |
| Talc | 3.00 mg |

The preparation of the film coated tablet is performed as described in Example 3.

What is claimed:

1. A pharmaceutical composition comprising
   L-2-amino-2,3,3-trideutero-3-(3,4-dihydroxyphenyl) propionic acid, or a physiologically acceptable salt thereof, having a deuterium enrichment above the natural abundance of deuterium; and
   L-2-amino-2,3-dideutero-3-(3,4-dihydroxyphenyl) propionic acid, or a physiologically acceptable salt thereof, having a deuterium enrichment above the natural abundance of deuterium.

2. The pharmaceutical composition of claim 1, wherein said deuterium enrichment above the natural abundance of deuterium is within a predefined range of 0.02 mol % to 100 mol % deuterium, as determined by NMR spectroscopy in $d_6$-dimethyl sulfoxide using a 500 MHz spectrometer.

3. The pharmaceutical composition of claim 1, wherein the L-2-amino-2,3,3-trideutero-3-(3,4-dihydroxyphenyl) propionic acid has the following formula:

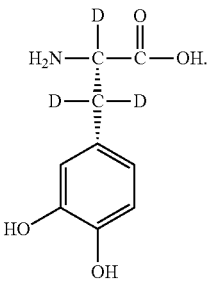

4. The pharmaceutical composition of claim 1, wherein the L-2-amino-2,3-dideutero-3-(3,4-dihydroxyphenyl) propionic acid has the following formula:

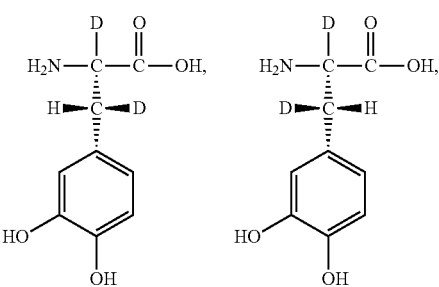

or a combination thereof.

5. The pharmaceutical composition of claim 1, wherein the L-2-amino-2,3-dideutero-3-(3,4-dihydroxyphenyl) propionic acid has the following formula:

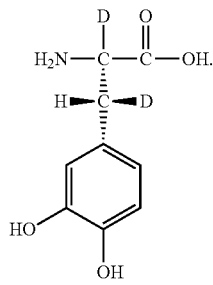

6. The pharmaceutical composition of claim 1, wherein the L-2-amino-2,3-dideutero-3-(3,4-dihydroxyphenyl) propionic acid has the following formula:

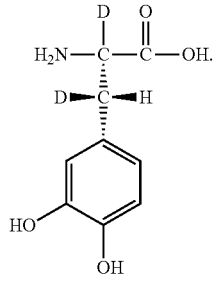

7. The pharmaceutical composition of claim 1, comprising 0.1 mol % to 99.9 mol % of the L-2-amino-2,3,3-trideutero-3-(3,4-dihydroxyphenyl) propionic acid.

8. The pharmaceutical composition of claim 6, comprising 5 mol % to 95 mol % of the L-2-amino-2,3,3-trideutero-3-(3,4-dihydroxyphenyl) propionic acid.

9. The pharmaceutical composition of claim 6, comprising 78 mol % to 95 mol % of the L-2-amino-2,3,3-trideutero-3-(3,4-dihydroxyphenyl) propionic acid.

10. The pharmaceutical composition of claim 6, comprising 88 mol % to 92 mol % of the L-2-amino-2,3,3-trideutero-3-(3,4-dihydroxyphenyl) propionic acid.

11. The pharmaceutical composition of claim 6, comprising 78 mol % to 82 mol % of the L-2-amino-2,3,3-trideutero-3-(3,4-dihydroxyphenyl) propionic acid.

12. The pharmaceutical composition of claim 1, comprising 90 mol % of the L-2-amino-2,3,3-trideutero-3-(3,4-dihydroxyphenyl) propionic acid and 10 mol % of the L-2-amino-2,3-dideutero-3-(3,4-dihydroxyphenyl) propionic acid.

13. The pharmaceutical composition of claim 1, comprising 80 mol % of the L-2-amino-2,3,3-trideutero-3-(3,4-dihydroxyphenyl) propionic acid and 20 mol % of the L-2-amino-2,3-dideutero-3-(3,4-dihydroxyphenyl) propionic acid.

14. The pharmaceutical composition of claim 1, comprising 85 mol % of the L-2-amino-2,3,3-trideutero-3-(3,4-dihydroxyphenyl) propionic acid and 15 mol % of the L-2-amino-2,3-dideutero-3-(3,4-dihydroxyphenyl) propionic acid.

15. The pharmaceutical composition of claim 1, comprising 70 mol % of the L-2-amino-2,3,3-trideutero-3-(3,4-dihydroxyphenyl) propionic acid and 30 mol % of the L-2-amino-2,3-dideutero-3-(3,4-dihydroxyphenyl) propionic acid.

16. The pharmaceutical composition of claim 1, wherein the deuterium enrichment in one β-position in the L-2-amino-2,3,3-trideutero-3-(3,4-dihydroxyphenyl) propionic acid is about 90 mol %.

17. The pharmaceutical composition of claim 16, wherein the deuterium enrichment in the α-position and the other β-position in the L-2-amino-2,3,3-trideutero-3-(3,4-dihydroxyphenyl) propionic acid is at least 98 mol %.

18. The pharmaceutical composition of claim 1, wherein the difference in the deuterium enrichment in the β-positions in the L-2-amino-2,3,3-trideutero-3-(3,4-dihydroxyphenyl) propionic acid is about 8 to 10 percentage points.

19. The pharmaceutical composition of claim 1, further comprising a pharmaceutically acceptable adjuvant or additive.

20. The pharmaceutical composition of claim 1, further comprising carbidopa, benserazide, or entacapone, or a mixture thereof.

21. A method of treating Parkinson's disease, restless leg syndrome, amyotrophic lateral sclerosis, or multiple system atrophy, comprising administering a pharmaceutical composition of claim 1 to a patient in need thereof.

22. The method of claim 21, for treating Parkinson's disease.

* * * * *